United States Patent [19]

Cook

[11] Patent Number: 5,145,984
[45] Date of Patent: Sep. 8, 1992

[54] BIS-SUCCINIMIDE DERIVATIVES

[75] Inventor: Stephen J. Cook, Burton Pidsea, England

[73] Assignee: BP Chemicals (Additives) Limited, London, England

[21] Appl. No.: 583,451

[22] Filed: Sep. 17, 1990

[30] Foreign Application Priority Data

Sep. 21, 1989 [GB] United Kingdom ............... 8921382

[51] Int. Cl.$^5$ .................. C07D 403/10; C07D 403/12
[52] U.S. Cl. .................................... 548/522; 548/520; 548/548; 548/546
[58] Field of Search ............................. 548/522, 520

[56] References Cited

U.S. PATENT DOCUMENTS

| | | | |
|---|---|---|---|
| 3,598,735 | 8/1971 | Wang | 548/520 |
| 3,718,663 | 2/1973 | Piasek et al. | 548/404 |
| 4,945,170 | 7/1990 | Kohli | 548/522 |

FOREIGN PATENT DOCUMENTS

| | | | |
|---|---|---|---|
| 746520 | 11/1966 | Canada | 548/520 |
| 0342823 | 11/1989 | European Pat. Off. | 548/522 |

*Primary Examiner*—David B. Springer
*Attorney, Agent, or Firm*—Brooks Haidt Haffner & Delahunty

[57] ABSTRACT

A process for producing a lubricating oil dispersant additive comprises:

step (1) reacting compound (A), wherein compound (A) is a hydrocarbyl-substituted or a substituted hydrocarbyl-substituted succinic acid or anhydride or ester thereof, with compound (B) of formula (I)

$$H_2N(CHR^1CHR^2O)_n CHR^3CHR^4NH_2 \qquad (I)$$

wherein one $R^2$ and $R^2$ is hydrogen and the other is hydrogen or a lower alkyl group and n is an integer from 1 to 10 and one of $R^3$ and $R^4$ is hydrogen and the other is hydrogen or a lower alkyl group, each of the —(CHR$^1$CH$^2$O)—units being independently defined, to give a product (C) and step(2) reacting product (C) with a diisocyanate (D) of formula (II)

$$OCN—R^5—NCO \qquad (II)$$

wherein $R^5$ is a divalent organic group. Novel succinimides have been prepared by the disclosed process, lubricating oil compositions comprise 1–20% w/w of the modified succinimdes. The succinimides have dispersancy and VI improver properties.

3 Claims, No Drawings

BIS-SUCCINIMIDE DERIVATIVES

This invention relates to modified succinimides, processes for making and compositions comprising said succinimides, in particular it relates to succinimides modified with diisocyanates.

Piston varnish and sludge formation are major problems in the operation of internal combustion engines. Accumulation of sludge in restricted parts of the engine can adversely affect the efficiency of the engine. To overcome sludge accumulation, it has traditionally been the practice to incorporate dispersant additives into the engine lubricating oil.

It is well known in the art to use nitrogen-containing compounds as dispersant additives in lubricating oils. For example U.S. Pat. No. 3,573,205 discloses the use of polyisobutenyl succinimides of alkylene polyamines modified with diisocyanates as lubricating oil dispersant additives. The diisocyanates are used as cross-linking agents to introduce urea functionalities and provide relatively high molecular weight compounds. We have found that lubricating oil dispersant additives derived from polyisobutenyl succinimides and cross-linked with diisocyanates can be prepared using polyoxyalkylene amines instead of or as well as polyamines.

According to the present invention there is provided a process for producing a lubricating oil dispersant additive which process comprises:

step (1) reacting compound (A), wherein compound (A) is a hydrocarbyl-substituted or a substituted hydrocarbyl-substituted succinic acid or anhydride or ester thereof, with compound (B) of formula (I)

$$H_2N(CHR^1CHR^2O)_nCHR^3CHR^4NH_2 \qquad (I)$$

wherein one of $R^1$ and $R^2$ is hydrogen and the other is hydrogen or a lower alkyl group and n is an integer from 1 to 10, and one of $R^3$ and $R^4$ is hydrogen and the other is hydrogen or a lower alkyl group each of the $-(CHR^1CHR^2O)-$ units being independently defined to give a product (C) and step (2) reacting product (C) with a diisocyanate (D) of formula (II)

$$OCN-R^5-NCO \qquad (II)$$

wherein $R^5$ is a divalent organic group.

Compound (A) may be a hydrocarbyl-substituted or substituted hydrocarbyl-substituted succinic anhydride or derivative thereof, the anhydride being characterised by the formula (III)

wherein $R^6$ is hydrocarbyl group (optionally substituted with halogen) for example an alkyl or alkenyl group preferably derived from a polyolefin, for example a polyolefin derived from a $C_2-C_8$ olefin preferably a $C_4-C_8$ olefin, and preferably a polyisobutene. The substituent $R^6$ may suitably have a number average molecular weight in the range from about 500 to about 3000, preferably from about 1000 to about 1500. $R^6$ may also be a succinic anhydride -substituted hydrocarbyl group or derivative thereof. Compound (A) in this case would contain two succinic anhydride groups or derivatives thereof. Compound (A) may suitably be the corresponding acid or ester derivative of any of the succinic anhydrides defined above. Compound (A) may comprise a mixture of any of the above defined compounds. For example Compound (A) may comprise a mixture of polyisobutenyl-substituted succinic anhydrides (PIBSA'S).

Compound (B) is a compound of formula (I)

$$H_2N(CHR^1CHR^2O)_nCHR^3CHR^4NH_2 \qquad (I)$$

wherein one of $R^1$ and $R^2$ is hydrogen and the other is hydrogen or lower alkyl, preferably $C_2-C_6$ alkyl, more preferably methyl, and n is an integer from 1 to 10 preferably 1 to 7, more preferably 2 to 7, one of $R^3$ and $R^4$ is hydrogen and the other is hydrogen or lower alkyl, preferably $C_2-C_6$ alkyl, more preferably methyl.

The product (C) formed in step (1) will comprise a succinimide. There is no requirement for product (C) to be isolated prior to reaction with (D). Step (1) will preferably be conducted under reaction conditions such that the product (C) of step (1) will comprise a significant proportion of a mono succinimide; therefore, since compound (B) is a diamine the product (C) will preferably comprise a proportion of primary amino groups. The primary amino groups in the product (C) are required so that the product (C) can be cross-linked with the diisocyanate (D) in step (2). The product (C) will preferably comprise at least one primary amino group per 2 molecules of said succinic acid or acid anhydride or ester reacted in step (1).

In step (2) the succinimide is reacted with an organic diisocyanate (D). Suitable organic diisocyanates may be represented by the formula (II)

$$OCN-R^5-NCO \qquad (II)$$

wherein $R^5$ is a group selected from alkylene, aralkylene, cycloalkylene, arylene, alkarylene, alkenylene and alkynylene groups; where $R^5$ is an alkylene group it is preferably a $C_2-C_{18}$, more preferably a $C_4-C_{12}$, alkylene group. An example of a suitable diisocyanate of the formula (II) is diisocyanatohexane (DIH) (where $R^5=-(CH_2)_6-$). Other suitable diisocyanates are 2,4-toluene diisocyanate and MDI (methylene diphenylene diisocyanate).

The ratio of the number of moles of succinic groups (anhydride, acid or ester) added to the number of moles of compound (B) added should be in the range 5:1 to 0.5:1 more preferably 2:1 to 1:1 for example 1.5:1 to 1.1:1. It is preferred that the succinic groups are added in a slight molar excess to compound (B) since excess amine in the final product may have a deleterious effect on engine seals. Where compound (A) comprises one succinic group, the number of moles of succinic groups added is equivalent to the number of moles of compound (A) added.

The ratio of the number of moles of compound (B) added to the number of moles of compound (D) added is preferably in the range 20:1 to 0.5:1, more preferably in the range 10:1 to 0.75:1, for example 4:1 to 1:1.

Excess diisocyanate may be destroyed by addition of primary amine after step (2). According to a further aspect of the present invention there is provided a process as defined hereinabove which further comprises addition of a primary amine RNH$_2$ for example where R=C$_2$-C$_6$ alkyl.

Steps (1) and (2) are preferably carried out in a high boiling inert solvent, suitably a high boiling hydrocarbon solvent. In view of the intended application of the product a preferred high boiling solvent is a lubricating oil. Natural or synthetic lubricating oils may be employed. Suitable lubricating oils include the solvent neutral (SN) oils.

The reaction is carried out at elevated temperature, suitably in the range from 40° to 220° C., preferably from 50° to 200° C. Step (1) as defined above is preferably carried out at a temperature in the range 100°-220° C. more preferably 140°-200° C. Step (2) as defined above is preferably carried out at a temperature in the range 40°-200° C. more preferably 60°-120° C.

Reaction of the primary amino groups of the succinimide of product (C) with the isocyanate groups of the diisocyanate (D) produces urea linkages.

According to a further aspect of the present invention there is provided a compound of formula (IV)

$$Q_2R^5 \quad (IV)$$

wherein Q is a group of formula (V)

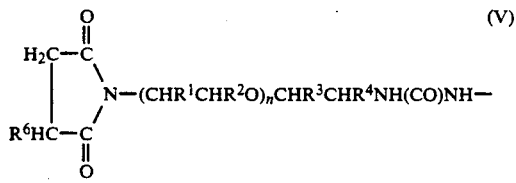

where R$^1$, R$^2$, R$^3$, R$^4$ and n are as defined in formula (I), R$^5$ is as defined in formula (II), R$^6$ is a hydrocarbyl or substituted hydrocarbyl group, each group Q being the same or different and each of the units —(CHR$^1$CHR$^2$O)— being independently defined.

Compounds of formula (IV) are products of the process as defined hereinabove and may be used as lubricating oil additives, in particular as dispersant additives and viscosity index improvers. An advantage of using compounds of the formula (IV) and products of the process as defined hereinabove, which are based upon polyoxyalkylene amines instead of compounds based upon polyamines is that solutions of those based upon polyamines are more stable at elevated temperatures than solutions of compounds of the formula (IV) or product of the process as defined hereinabove.

In another aspect, the present invention provides a lubricating oil composition comprising a major portion of a lubricating oil and a minor portion of a product produced by the process as hereinabove defined, or a compound of the formula (IV).

The lubricating oil composition will contain 1-20% w/w preferably 4-10% w/w more preferably 5-7% w/w of said product or compound of formula IV.

Lubricating oils useful in the compositions of the invention may be any natural or synthetic lubricating oil.

The lubricating oil composition hereinabove defined may further comprise conventional additives, for example one or more of anti-wear additives, antioxidants, anti-rust additives and viscosity index improvers. It is an advantage of the present invention, that additives produced by the process of the present invention also have viscosity index improving properties. Consequently at least some of the VI improver additive conventionally present in lubricating oil compositions may be omitted.

The invention will now be further illustrated by reference to the following Examples.

COMPARATIVE EXAMPLE

To a 50% solution of a succinimide (prepared by reacting a polyisobutene succinic anhydride of average Mn 1800 and tetraethylene pentamine (TEPA)) in SN150 base oil at 80° C. was added, with stirring, DIH (in a 1:1 molar ratio with the succinimide groups) dropwise over 15 minutes. Reaction was continued for 1.5 hours with stirring.

The product was dissolved in further SN150 oil sufficient to produce a 6.5% level of active components (active components are defined as everything in the reaction mixture other than the SN150 oil) and its viscometric behaviour examined. The viscometric results are given in Table 1.

EXAMPLE 1

Step (1)

Polyisobutylene succinic anhydride (PIBSA), (derived from a 40:60 molar mixture of polyisobutylene succinic anhydrides of Mn 1000 and Mn 2400, 840 g) and "Jeffamine 148" (1,2 bis(amino-ethoxy)ethane, from Texaco Chemicals, 53.4 g) were heated at 180° C. for 4 hr, the final hour of which was under reduced pressure at 10 mm Hg.

Step (2)

To a 50% solution of the product from step 1 in SN150 base oil at 60° C. was added, with stirring, diisocyanatohexane (DIH, 1 mole of isocyanate groups per 1 mole of succinimide group) dropwise over 10 minutes. Reaction was continued for 5 hr.

The product from step (2) was dissolved in further SN150 oil sufficient to produce 7.3% level of active components and its viscometric behaviour examined. The viscometric results are given in Table I.

EXAMPLE 2

The procedure of example 1 was followed except that in step (2) the reaction was carried out at 180° C., and 2 moles of isocyanate groups to 1 mole of succinimide groups were used.

EXAMPLE 3

The procedure of example 1 was followed except that in step (2) the reaction was carried out at 100° C. for 2 hr and 1.5 moles of isocyanate groups to 1 mole of succinimide groups were used.

EXAMPLE 4

The procedure of example 3 was followed except that the product from step (2) was treated with hexylamine to destroy excess isocyanate.

EXAMPLE 5

The procedure of example 3 was followed except that in step (2) 1 mole of isocyanate groups to 1 mole of succinimide groups was used.

EXAMPLE 6

The procedure of example 3 was followed except that in step (2) 0.75 moles of isocyanate groups to 1 mole of succinimide groups were used.

EXAMPLE 7

Step (1)

The procedure of example 1 step (1) was used except that the PIBSA (420 g) was reacted with "Jeffamine D230" (from Texaco Chemicals, 41.5 g).

Step (2)

The procedure of example 3 step (2) was followed using the succinimide from step (1) above.

EXAMPLE 8

The procedure of example 6 was followed except that the succinimide from example 7 step (1) was used and step (2) was carried out at 120° C. for 5 hr.

EXAMPLE 9

Step (1)

The procedure of example 1 step (1) was used except that the PIBSA (420 g) was reacted with "Jeffamine D400" (from Texaco Chemicals, 72.2 g).

Step (2)

The procedure of example 3 step (2) was followed using the succinimide from step (1) above.

EXAMPLE 10

The procedure of example 5 was followed except that the succinimide from example 9 step (1) was used and the reaction was carried out for 6 hr.

Jeffamine D230 is a mixture of compounds of formula (I) $H_2N[CH_2CH(CH_3)O]_nCH_2CH(CH_3)NH_2$ where n=3,4 and 5. Jeffamine D400 is a mixture of compounds of the same formula as D230 except where n=6, and 7.

Table I illustrates the viscometric results for the above examples. Some examples have results at two concentration levels, and some examples were tested after storage at 100° C. for specified periods.

TABLE 1

| | Active Components | Viscosity at Specific Temperatures | | | |
|---|---|---|---|---|---|
| | CONC % w/w | 100° C. cSt | 40° C. cSt | −20° C. P | VI |
| EXAMPLE 1 | 7.3 | 8.52 | 54.9 | 43.0 | 130 |
| | 6.5 | 7.83 | 49.9 | 39.0 | 125 |
| (3 days at 100C) | 6.5 | 8.01 | 50.7 | 39.0 | 128 |
| EXAMPLE 2 | 7.3 | 8.22 | 54.3 | 43.0 | 122 |
| EXAMPLE 3 | 7.3 | 8.93 | 60.9 | 39.0 | 123 |
| | 6.5 | 8.37 | 55.5 | 36.0 | 123 |
| (3d at 100C) | 6.5 | 10.56 | 64.2 | 38.5 | 154 |
| EXAMPLE 4 | 6.5 | 8.89 | 56.7 | 38.5 | 134 |
| (3d at 100C) | 6.5 | 9.11 | 57.3 | 38.0 | 139 |
| EXAMPLE 5 | 6.5 | 8.78 | 64.5 | 36.5 | 109 |
| (3d at 100C) | 6.5 | 9.88 | 62.7 | 38.5 | 141 |
| EXAMPLE 6 | 6.5 | 8.85 | 59.1 | 41.0 | 123 |
| (3d at 100C) | 6.5 | 9.13 | 60.3 | 38.5 | 130 |
| EXAMPLE 7 | 7.3 | 8.09 | 59.6 | 39.0 | 103 |
| (3d at 100C) | 6.5 | 8.46 | 53.3 | 39.0 | 133 |

TABLE 1-continued

| | Active Components | Viscosity at Specific Temperatures | | | |
|---|---|---|---|---|---|
| | CONC % w/w | 100° C. cSt | 40° C. cSt | −20° C. P | VI |
| EXAMPLE 8 | 6.5 | 7.94 | 51.5 | 38.5 | 122 |
| EXAMPLE 9 | 7.3 | 8.23 | 61.8 | 38.5 | 101 |
| (3d at 100C) | 6.5 | 8.78 | 56.4 | 37.5 | 132 |
| EXAMPLE 10 | 6.5 | 8.25 | 54.5 | 36.0 | 123 |
| COMP. | 6.5 | 8.70 | 54.8 | 39.5 | 135 |
| EXAMPLE | 5.5 | 8.35 | 51.5 | | 136 |
| (4d at 100C) | 5.5 | 7.94 | 49.9 | | 128 |
| (11d at 100C) | 5.5 | 7.70 | 48.9 | | 124 |

BENCH DISPERSANCY TEST DATA

Dispersants were examined by a TLC method involving doping of solutions of dispersants in oil with used oil. The results are expressed as a value obtained by multiplying the percentage streak length by the percentage of material moved from the origin. The higher the value, the better the dispersant.

RESULTS

Material from example 3 step (2)  6100
Material from example 7 step (2)  5355
Material from example 9 step (2)  3634
Material from comparative example  926

I claim:

1. A compound of formula (IV)

$$Q_2R^5 \quad (IV)$$

wherein Q is a group of formula (V)

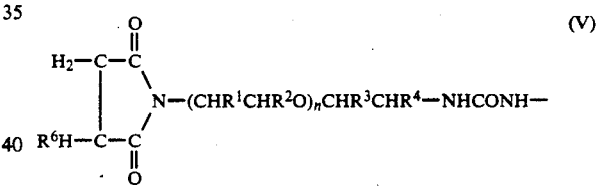

(V)

wherein one of $R^1$ and $R^2$ is hydrogen and the other is hydrogen or a lower alkyl group and n is an integer from 1 to 10 and one of $R^3$ and $R^4$ is hydrogen and the other is hydrogen or a lower alkyl group, $R^5$ is a divalent radical selected from the group consisting of alkylene, aralkylene, cycloalkylene, arylene, alkarylene, alkenylene and alkynylene, and $R^6$ is a hydrocarbyl or substituted hydrocarbyl group, each group Q being the same or different, and each of the units—$(CHR^1CHR^2O)$ being independently defined.

2. A compound as claimed in claim 1 wherein $R^6$ is an alkyl or alkenyl group having a number average molecular weight in the range from about 500 to about 3,000.

3. A compound as claimed in claim 1 or claim 2 wherein n is an integer from 2 to 7, $R^1$ and $R^3$ are each hydrogen and $R^2$ and $R^4$ are each methyl.

* * * * *

UNITED STATES PATENT AND TRADEMARK OFFICE
CERTIFICATE OF CORRECTION

PATENT NO. : 5,145,984

DATED : September 8, 1992

INVENTOR(S) : STEPHEN J. COOK

It is certified that error appears in the above-identified patent and that said Letters Patent is hereby corrected as shown below:

Abstract, line 8, "one $R^2$ and $R^2$" should read --one of $R^1$ and $R^2$--.

Abstract, line 12, $(CHR^1CH^2O)$ should read --$(CHR^1CHR^2O)$--.

Signed and Sealed this

Fifth Day of October, 1993

*Attest:*

BRUCE LEHMAN

*Attesting Officer*     *Commissioner of Patents and Trademarks*